United States Patent [19]
Helmy

[11] Patent Number: 5,370,613
[45] Date of Patent: Dec. 6, 1994

[54] CATHETER APPARATUS FOR DELIVERING DRUGS TO THE PENIS

[76] Inventor: Ali M. Helmy, Bokami Blg., Flat 304, Palestine St., Jeddah 18840/21414, Saudi Arabia

[21] Appl. No.: 16,235

[22] Filed: Feb. 11, 1993

[51] Int. Cl.$^5$ .............................................. A61M 11/00
[52] U.S. Cl. ...................................... 604/93; 604/264; 604/280
[58] Field of Search ...................... 604/93, 51, 53, 117, 604/244, 264, 280; 606/170; 623/12

[56] References Cited
U.S. PATENT DOCUMENTS

| | | | |
|---|---|---|---|
| 4,586,921 | 5/1986 | Beison | 604/49 |
| 4,801,297 | 1/1989 | Mueller | 604/264 |
| 4,863,426 | 9/1989 | Ferragamo et al. | 604/93 |
| 4,936,826 | 6/1990 | Amarasinghe | 604/53 |
| 5,071,404 | 12/1991 | Larkin et al. | 604/244 |

*Primary Examiner*—C. Fred Rosenbaum
*Assistant Examiner*—N. Kent Gring
*Attorney, Agent, or Firm*—Vorys, Sater, Seymour & Pease

[57] ABSTRACT

An implantable catheter apparatus for self-administration of drugs to the penis of a human patient comprises
  an elongated catheter having a flexible wall surrounding a lumen
  the catheter having
    a distal portion having a closed distal end and adapted to be placed within the corpus cavernosum of the penis of a human patient,
    a proximal portion adapted to be implanted in the body of the patient at a location remote from the penis, and
    an intermediate portion connecting the proximal and distal portions and adapted to be implanted within the body of said patient,
  resealable injection port means located at the proximal end providing fluid access from a source of fluid to the lumen,
  the distal portion of the catheter being provided with longitudinal slits to permit fluid to flow from the lumen to the exterior of said catheter.

In one embodiment of the invention the slits are staggered longitudinally along the wall of the catheter at different distances from the closed end with longitudinal overlap, while in another embodiment the catheter is provided with a sheath surrounding the wall and covering the slits.

17 Claims, 3 Drawing Sheets

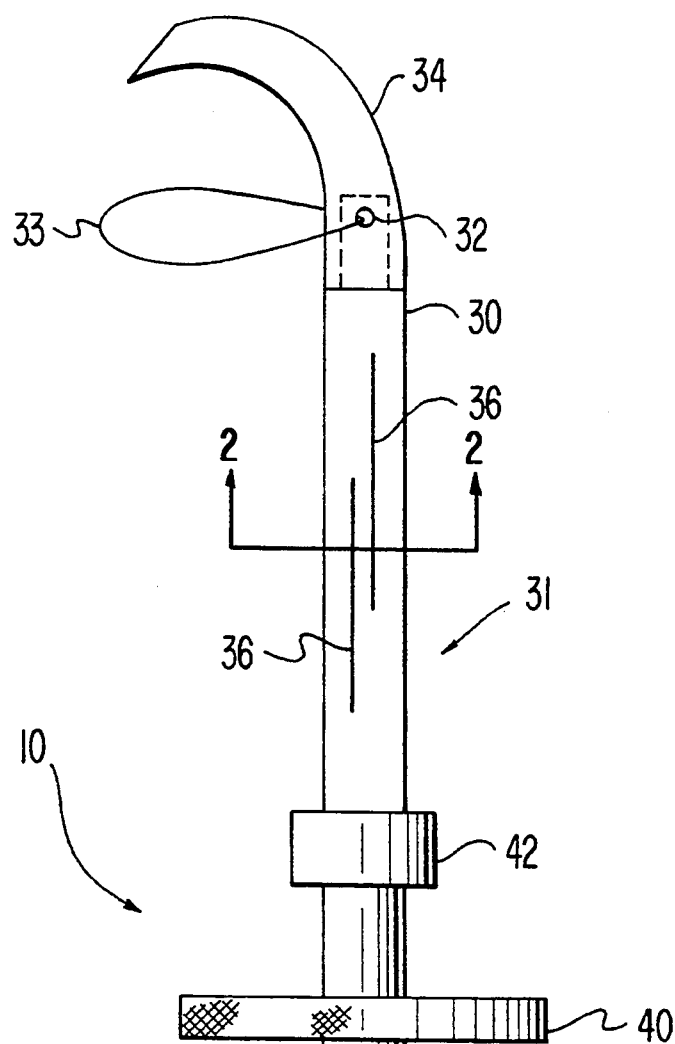
FIG. 1
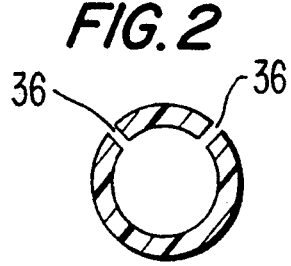
FIG. 2
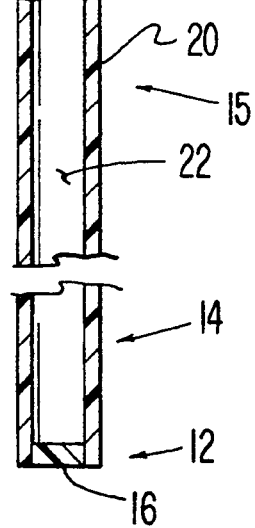

CATHETER APPARATUS FOR DELIVERING DRUGS TO THE PENIS

BACKGROUND OF THE INVENTION

1. Field of the invention

This invention relates generally to a device for use in the treatment of men afflicted with impotence. More particularly, it relates to an improved apparatus for self-administration to the penis of drugs that can provoke an erection.

2. Brief Summary of the Prior Art

Administration of vasodilator drugs directly to the penis has been investigated as a method for treating penile erectile dysfunction. However, inasmuch as the procedure requires inserting a needle into the base of the penis, the procedure tends to be both frightening and painful to the patient. Furthermore, repeated administration of drugs by direct injection can lead to undesirable side effects such as hematoma, infection and eventually fibrosis. An additional problem is the reluctance of some patients to administer the drugs to themselves. Consequently, they have the injections made at clinics with the accompanying evident obstacles to convenient or normal sexual relations.

Accordingly, a need has continued to exist for a safe, effective, painless and convenient method for a patient afflicted with impotence to inject himself with a vasoactive drug to achieve a normal erection without risking the side effects of local injection.

SUMMARY OF THE INVENTION

This need has now been alleviated by the device of this invention, which is an implantable catheter apparatus for self-administration of drugs to the penis of a human patient comprising an elongated catheter having a flexible wall surrounding a lumen the catheter having a distal portion having a closed distal end and adapted to be placed within the corpus cavernosum of the penis of a human patient, a proximal portion adapted to be implanted in the body of said patient at a location remote from said penis, and an intermediate portion connecting said proximal and said distal portions and adapted to be implanted within the body of said patient, resealable injection port means located at the proximal end providing fluid access from a source of fluid to the lumen, the distal portion of the catheter being provided with longitudinal slits to permit fluid to flow from the lumen to the exterior of said catheter.

In one embodiment of the invention the slits are staggered longitudinally along the wall of the catheter at different distances from the closed end with longitudinal overlap.

In another embodiment of the invention the catheter is provided with a sheath surrounding the wall and covering the slits.

Accordingly, it is an object of the invention to provide an improved drug delivery apparatus for the treatment of impotence.

A further object is to provide an improved drug delivery device for parenteral self-administration of drugs.

A further object is to provide a drug delivery device for self-administration of drugs to the penis.

A further object is to provide a drug delivery device for parenteral administration of drugs to the penis from a remote injection site.

Other objects of the invention will become apparent from the following detailed description when considered in conjunction with the drawings.

BRIEF DESCRIPTION OF THE DRAWINGS

FIG. 1 is a side view, partially cut away, of one embodiment of the drug delivery catheter of the invention.

FIG. 2 is a cross-sectional view of the catheter of the invention taken along section 2—2 in FIG. 1.

DETAILED DESCRIPTION OF THE INVENTION AND PREFERRED EMBODIMENTS

Figure 3:
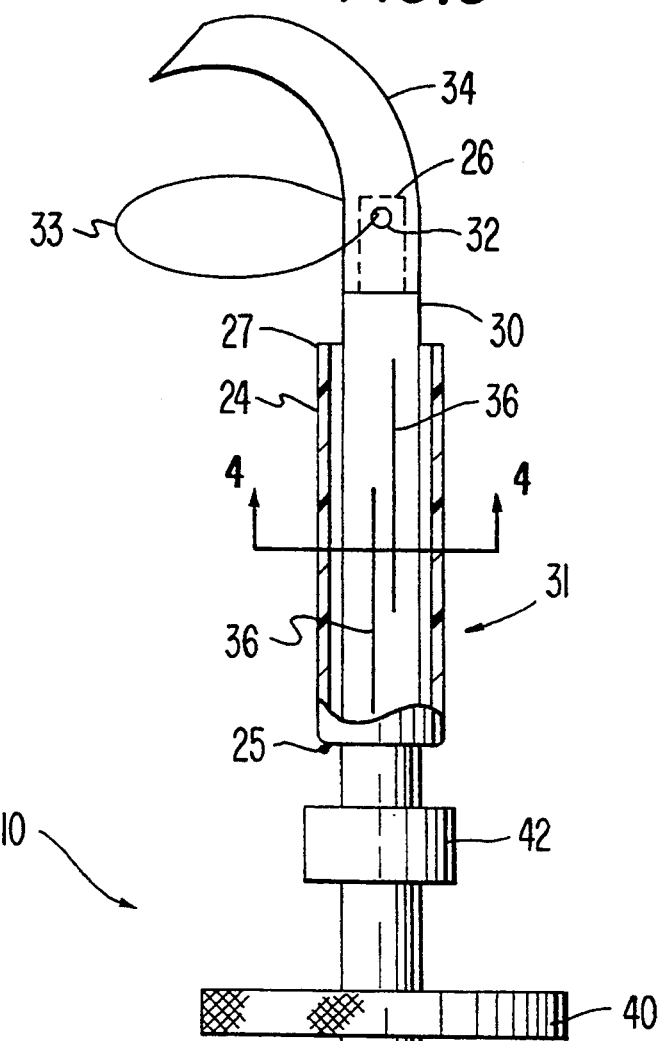
FIG. 3 is a side view, partially cut away, of another embodiment of the drug delivery catheter of the invention.

One embodiment of the drug delivery catheter of the invention is illustrated in FIGS. 1 and 2. The catheter 10 comprises a distal portion 31 adapted to be implanted in the corpus cavernosum of the penis, a proximal portion 14 adapted to be implanted subcutaneously at a site remote from the penis, and an intermediate portion 15 extending within the body of the patient between the distal portion and the proximal portion. The proximal portion 14 of the catheter 10 terminates in a proximal end 12 which is typically implanted in the upper lateral portion of the gluteal region of the patient.

The proximal end 12 of the catheter 10 is provided with self-sealing injection port means through which a drug in a liquid vehicle may be introduced into the catheter and forced through the lumen to the penis. Such self-sealing ports are known, and it is according to the invention to employ any conventional self-sealing port designed to be implanted for repetitive parenteral administration of drugs and the like. By way of example only, in FIG. 1 the self-sealing means is shown as a conventional pierceable septum 16 made of rubber or the like material which can be pierced by a hypodermic needle for injection of drug in a liquid vehicle from a syringe into the lumen of the catheter, and which seals the injection opening when the needle is withdrawn. Such self-sealing input ports may be provided with a perforated backing plate (not shown), made, e.g., of stainless steel, to prevent the needle from piercing the patient's tissue or delicate parts of the catheter. In practice any conventional self-sealing port and corresponding fluid injection means for introducing a liquid through the port may be used in the apparatus of the invention. A suitable resealable device is shown, for example, in U.S. Pat. No. 4,261,357.

The catheter itself comprises a flexible wall 20 surrounding a lumen 22. The wall may be made of any biocompatible material that is suitable for implantable catheters. For example, the wall may be made of any flexible biocompatible synthetic plastic, natural or synthetic rubber, or silicone rubber. The exterior surface should be generally smooth and devoid of sharp edges that might injure the patient. The external diameter of the catheter will typically be about 7 French while the diameter of the lumen will be about 3 French.

The distal portion 31 of the catheter 10 is adapted to be placed within the corpus cavernosum of the penis. The distal end 30 of the catheter is closed, and is provided with a short extension 26 having a transverse hole 32. A curved blade 34 is attached to the distal end 30 of the catheter 10 by means of a hollow shank that fits over the extension 26 and is a provided with a transverse hole capable of registering with the transverse hole 32 in the extension 26. A thread 33 is looped through the hole in the shank of the blade and the transverse hole 32 in the extension 26 to fix the blade to the catheter. It will be understood that the catheter of FIG. 1 is a preferred embodiment, and that the blade 34 and means for attaching it to the tip 31 of the catheter are preferred elements useful for the convenient implantation of the catheter but are not necessary for its function.

The distal portion 31 of the catheter 10 is provided with a plurality of slits 36 extending in a generally longitudinal direction. The slits 36 extend through the entire thickness of the wall 20 and provide a means for fluid within the lumen 22 to flow out of the catheter into the tissue surrounding the distal portion 31 of the catheter. The slits are normally held closed by reason of the elastic properties of the material from which the wall 20 is made, thereby preventing flow of fluid from the tissue surrounding the catheter into the lumen 20. The slits are positioned at different distances from the distal end 30 of the catheter whereby adjacent slits have an overlapping staggered configuration. This arrangement helps to assure that the slits 36 remain normally closed even if the catheter becomes flexed or kinked in that region. However, when the wall 20 of the catheter 10 is distended by pressure within the lumen 22 due to the introduction of a liquid vehicle containing a drug, the slits open slightly, as shown in the cross-section FIG. 2, and allow the liquid vehicle with its drug to enter the penis. The elongated slits also promote a relatively even distribution of the drug within the penis.

The distal portion 31 of the catheter 10 is fixed within the corpus cavernosum by means of a discoid cuff 40 fastened to the outer surface of the catheter wall 20 at an appropriate distance from the end of the catheter. The cuff 40 is designed to be sutured to the fascia surrounding the corpus cavernosum. To this end it is preferably made from a woven polyester scrim impregnated with a silicone rubber material. Any equivalent structure or material will also be suitable for the cuff. The catheter is also provided with a toroidal node 42 on the outer surface of the wall 20 of the catheter just distal to the discoid cuff 40. When the distal portion 31 of the catheter has been positioned within the corpus cavernosum the node 42 is located just within the fascia.

Figure 4:
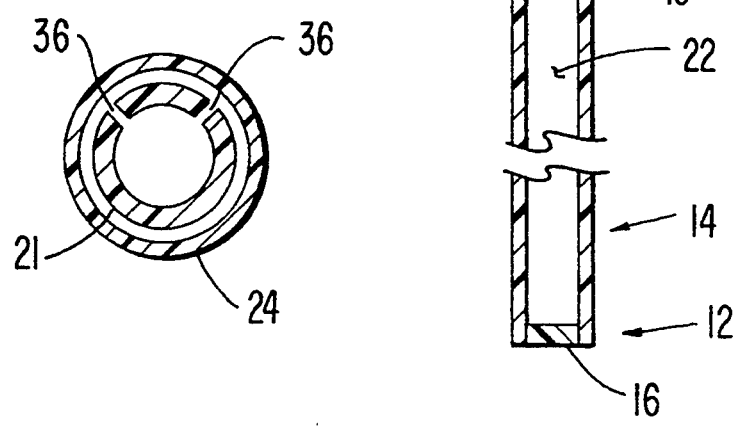
FIG. 4 is a cross-sectional view of the embodiment of the invention illustrated in FIG. 3, taken along section 4—4 in FIG. 1.

In another embodiment of the invention illustrated in FIGS. 3 and 4, a close-fitting sheath 24 surrounds the slits 36 in the distal portion 31 of the catheter apparatus 10. The sheath 24 has a proximal end 25 which is fastened to the wall 20 of the catheter just proximal to the slits 36. The sheath extends distally to cover the slits, and terminates in a distal end 27 distal to the slits, but not sealed to the wall 20 of the catheter. Thus, the drug in its vehicle can flow out of the slits 36 and out between the wall 20 of the catheter and the distal end 27 of the sheath 24 into the corpus cavernosum. The sheath 24 helps to prevent the slits 36 from becoming plugged with tissue. In the embodiment of the catheter 10 that incorporates the sheath 24 the slits 36 may be placed in a staggered configuration but do not have to be in a staggered configuration. Furthermore, in the embodiment of the catheter 10 that incorporates the sheath 24 a single slit 36 may suffice to permit the flow of fluid from the interior to the exterior of the catheter.

Figure 5:
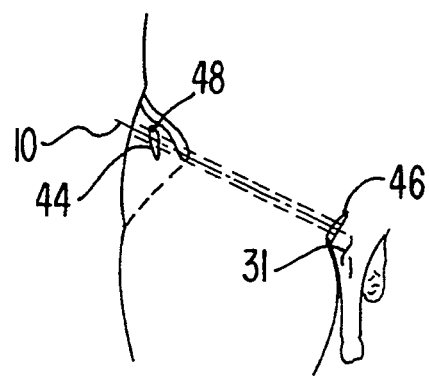
FIGS. 5 and 6 are diagrammatic views illustrating the implantation of the catheter of the invention.
Figure 6:
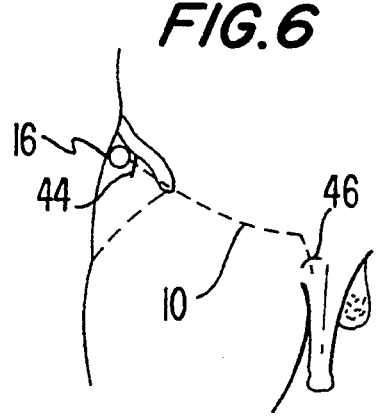

The catheter of this invention may be implanted by a surgical procedure conducted as follows and illustrated in FIGS. 5 and 6. The patient is placed under general or local anesthetic. A semicircular incision 44 is made in the upper outer quadrant of the gluteal region of the patient, as shown in FIG. 5. The gluteal fascia is opened by blunt dissection and space is created to accommodate the self-sealing injection port means located at the proximal end of the catheter. An incision 46 is made at the root of the penis and a metal tube or trocar 48 is passed subcutaneously between the two incisions. The site of anastomosis with the corpus cavernosum is prepared by separating and cutting the fascia. The tip of the catheter is then introduced into the corpus cavernosum either through a hole made by a separate procedure immediately before introducing the catheter or by inserting the blade attached to the tip of the catheter. The tip of the catheter with blade attached is then passed distally within the corpus cavernosum for a distance of about 2.5 centimeters, and then the blade is directed out through the wall of the penis. The catheter is then pulled by the now accessible distal end until the until the cuff of the catheter lies adjacent to the fascia. The cuff is then sutured continuously around the hole and secured in place. The blade is then removed, the tip of the catheter is tucked back inside the corpus cavernosum and the exit wound is closed and sutured.

The proximal end of the catheter is then passed through the trocar 48 from the end nearest the penis to the gluteal end. Once the proximal end 12 of the catheter is available at the gluteal end of the trocar, the trocar itself can be removed. The proximal end of the catheter is then cut off, leaving just enough for joining to the injection port means. The injection port is then attached, either directly or through a short cannula, depending on the particular type of injection port being used. The injection port means is oriented to avoid kinking the catheter and is fixed in place by non-absorbable sutures. In obese patients it can be placed subcutaneously. Normal saline is injected though the injection port to affirm patency of the catheter before the incisions are closed. The final disposition of the catheter after implantation is shown in FIG. 6.

During the first three postoperative weeks the patient is taught self-injection with physiological saline only. At a later stage the vasoactive drugs (papaverine hydrochloride and phentolamine mesylate in the ratio of 30:1 by weight) are injected under medical supervision. The prescribed dose is 7.5 milligrams of papaverine HCl combined with 0.25 milligrams of phentolamine mesylate or multiples thereof. Other safe and effective drugs capable of producing the same physiological effect, either known at present or which may become known in the future, may be used in place of the papaverine HCl—phentolamine mesylate combination.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

I claim:

1. An implantable catheter apparatus for self-administration of drugs to the penis of a human patient comprising a catheter having
a flexible wall surrounding a lumen,
a distal portion adapted to be placed within the corpus cavernosum of the penis of a human patient, said distal portion having a closed distal end,
a proximal portion adapted to be implanted in the body of said patient at a location remote from said penis, said proximal portion having a proximal end, and
an intermediate portion connecting said proximal and said distal portions and adapted to be implanted within the body of said patient, and
resealable injection port means located at said proximal end providing fluid access from a source of fluid to said lumen,
said distal portion of said catheter having a plurality of longitudinal slits piercing said wall of said catheter, said slits being at different distances from said distal end of said catheter such that adjacent slits have an overlapping staggered configuration.

2. The catheter apparatus of claim 1 additionally comprising a circumferential close-fitting sheath covering said slits, said sheath having a proximal end attached to the outer surface of said catheter proximal to said slits, and a free distal end positioned distally of said slits.

3. The catheter of claim 2 wherein said distal end of said catheter is provided with a transverse hole that does not intersect the lumen of said catheter.

4. The catheter of claim 2 additionally comprising flexible cuff means located near said distal end for suturing said catheter to surrounding tissues.

5. The catheter of claim 4 additionally comprising a circumferential node located distally of said cuff.

6. The catheter of claim 2 containing a pair of said slits.

7. The catheter of claim 2 wherein said slits have a length of about 5 millimeters.

8. The catheter of claim 2 wherein said port means comprises a pierceable septum sealing said proximal end of said lumen.

9. The catheter of claim 2 additionally comprising a blade member removably secured to said distal end.

10. An implantable catheter apparatus for self-administration of drugs to the penis of a human patient comprising a catheter having
a flexible wall surrounding a lumen,
a distal portion adapted to be placed within the corpus cavernosum of the penis of a human patient, said distal portion having a closed distal end,
a proximal portion adapted to be implanted in the body of said patient at a location remote from said penis, said proximal portion having a proximal end, and
an intermediate portion connecting said proximal and said distal portions and adapted to be implanted within the body of said patient, and
resealable injection port means located at said proximal end providing fluid access from a source of fluid to said lumen,
said distal portion of said catheter having at least one longitudinal slit piercing said wall of said catheter,
said catheter apparatus additionally comprising a circumferential close-fitting sheath covering said slit,
said sheath having a proximal end attached to the outer surface of said catheter proximal to said slit, and a free distal end positioned distally of said slit.

11. The catheter of claim 10 wherein said distal end of said catheter is provided with a transverse hole that does not intersect the lumen of said catheter.

12. The catheter of claim 10 additionally comprising flexible cuff means located near said distal end for suturing said catheter to surrounding tissues.

13. The catheter of claim 12 additionally comprising a circumferential node located distally of said cuff.

14. The catheter of claim 10 containing a pair of said slits.

15. The catheter of claim 14 wherein said slits have a length of about 5 millimeters.

16. The catheter of claim 12 wherein said port means comprises a pierceable septum sealing said proximal end of said lumen.

17. The catheter of claim 12 additionally comprising a blade member removably secured to said distal end.

* * * * *